United States Patent [19]

Gulliver et al.

[11] Patent Number: 5,567,839

[45] Date of Patent: Oct. 22, 1996

[54] PROCESS FOR THE PREPARATION OF VINYL ACETATE

[75] Inventors: David J. Gulliver, Banstead; Simon J. Kitchen, Doncaster, both of England

[73] Assignee: BP Chemicals Limited, London, England

[21] Appl. No.: 342,314

[22] Filed: Nov. 18, 1994

[30] Foreign Application Priority Data

Nov. 19, 1993 [GB] United Kingdom .................. 9323823
Nov. 19, 1993 [GB] United Kingdom .................. 9323857

[51] Int. Cl.$^6$ ............................................ C07C 67/05
[52] U.S. Cl. ........................... 560/245; 502/169; 502/243
[58] Field of Search ................................................. 560/245

[56] References Cited

U.S. PATENT DOCUMENTS

| | | |
|---|---|---|
| 3,743,607 | 7/1973 | Sennewald et al. . |
| 3,775,342 | 11/1973 | Kronig .................. 560/245 |
| 3,822,308 | 7/1974 | Kronig et al. . |
| 3,939,199 | 2/1976 | Fernholz et al. . |
| 4,048,096 | 9/1977 | Bissot . |
| 4,087,622 | 5/1978 | Nakamura et al. . |
| 4,093,559 | 6/1978 | Fernholz et al. . |
| 4,119,567 | 10/1978 | Bartsch . |
| 4,158,737 | 6/1979 | Bartsch . |
| 4,347,383 | 8/1982 | Isshiki .................. 564/249 |
| 4,370,261 | 1/1983 | Wunder et al. . |
| 4,370,492 | 1/1983 | Wunder et al. . |
| 4,407,733 | 10/1983 | Birkenstock .......... 502/174 |
| 4,550,097 | 10/1985 | Drake . |
| 4,668,819 | 5/1987 | Fernholz et al. . |
| 4,902,823 | 2/1990 | Wunder et al. . |
| 5,179,056 | 1/1993 | Bartley . |
| 5,179,057 | 1/1993 | Bartley . |
| 5,185,308 | 2/1993 | Bartley et al. . |
| 5,189,004 | 2/1993 | Bartley et al. . |
| 5,225,388 | 7/1993 | Wunder et al. . |
| 5,250,487 | 10/1993 | Wirtz et al. . |
| 5,274,181 | 12/1993 | Bartley et al. . |
| 5,292,931 | 3/1994 | Wirtz et al. . |
| 5,342,987 | 8/1994 | Bartley . |
| 5,347,046 | 9/1994 | White .................... 560/245 |

FOREIGN PATENT DOCUMENTS

| | | |
|---|---|---|
| 1156674 | 11/1983 | Canada . |
| 2071698 | 12/1992 | Canada . |
| 2093610 | 10/1993 | Canada . |
| 563414 | 3/1992 | European Pat. Off. . |
| 519435 | 12/1992 | European Pat. Off. . |
| 519436 | 12/1992 | European Pat. Off. . |
| 565952 | 10/1993 | European Pat. Off. . |
| 2121693 | 8/1972 | France . |
| 1283737 | 8/1972 | United Kingdom . |
| 1288299 | 9/1972 | United Kingdom . |
| 1333449 | 10/1973 | United Kingdom . |
| 1500167 | 2/1978 | United Kingdom . |
| 1511869 | 5/1978 | United Kingdom . |

*Primary Examiner*—Michael L. Shippen
*Attorney, Agent, or Firm*—Fay, Sharpe, Beall, Fagan, Minnich & McKee

[57] ABSTRACT

In a process for the preparation of palladium and palladium/gold shell type catalysts for vinyl acetate production, the improvement comprises using a barium salt to precipitate water-insoluble palladium and optional gold compounds onto a support prior to reduction with a reducing agent. A barium salt additive may also be introduced to the catalyst after reduction to reduce the tendency of the catalyst to deactivate with use.

15 Claims, 5 Drawing Sheets

PROCESS FOR THE PREPARATION OF VINYL ACETATE

The present invention relates to the preparation of catalysts and in particular to the preparation of palladium and palladium/gold catalysts useful in effecting the production of vinyl acetate from ethylene, acetic acid and oxygen containing gas.

The production of vinyl acetate by reacting ethylene, acetic acid and oxygen together in the gas-phase in the presence of a catalyst containing palladium, gold and an alkali metal acetate promoter is a known process. The catalyst components are typically supported on a porous carrier material such as silica or alumina.

In early examples of these catalysts, both the palladium and gold were distributed more or less uniformly throughout the carrier (see for example U.S. Pat. No. 3,743,607 and GB 1,333,449). This was subsequently recognised to be a disadvantage because it was found that the material within the inner part of the carrier did not contribute to the reaction since the reactants did not diffuse significantly into the carrier before reaction occurred. In other words a significant amount of the palladium and gold never came into contact with the reactants.

In order to overcome this problem, new methods of catalyst manufacture were devised with the aim of producing catalysts in which the most active components were concentrated in the outermost shell of the support (shell impregnated catalysts). For example GB 1,500,167 claims catalysts in which at least 90% of the palladium and gold is distributed in that part of the carrier particle which is not more than 30% of the particle radius from the surface, whilst GB 1,283,737 teaches that the degree of penetration into the porous carrier can be controlled by pretreating the porous carrier with an alkaline solution of, for example, sodium carbonate or sodium hydroxide.

Another approach which has been found to produce particularly active catalysts is described in U.S. Pat. No. 4,048,096. In this patent, shell impregnated catalysts are produced by a process comprising the Steps of (1) impregnating a catalyst support with an aqueous solution of water-soluble palladium and gold compounds, the total volume of the solutions being 95 to 100% of the absorptive capacity; (2) precipitating water-insoluble palladium and gold compounds on the catalyst support by contacting the impregnated catalyst support with a solution of alkali metal silicate, the amount of alkali metal silicate being such that, after the alkali metal silicate has been in contact with the carrier for 12 to 24 hours, the pH of the solution is from 6.5 to 9.5; (3) converting the water-insoluble palladium and gold compounds into palladium and gold metal by treatment with a reducing agent; (4) washing with water; (5) contacting the catalyst with alkali metal acetate and (6) drying the catalyst.

U.S. Pat. No. 5,185,308 describes the preparation of palladium/gold shell impregnated catalysts for vinyl acetate production which are prepared by a series of steps including impregnation, precipitation, reduction, washing, drying, potassium acetate loading and final drying. The use of alkali metal salts such as sodium metasilicate and sodium hydroxide as precipitating agents is described therein.

The use of sodium, lithium and potassium silicates and hydroxides as precipitating agents is described in U.S. Pat. No. 5,179,056, U.S. Pat. No. 5,189,004 and U.S. Pat. No. 5,179,057.

The use of alkali metal acetates, in particular potassium acetate, as promoters for both non-shell and shell type catalysts for vinyl acetate production is known (see for example, U.S. Pat. No. 3,743,607; U.S. Pat. No. 3,822,308; U.S. Pat. No. 4,087,622; U.S. Pat. No. 5,179,056; U.S. 5,185,308; U.S. Pat. No. 5,179,057; U.S. Pat. No. 5,189,004 and U.S. Pat. No. 5,250,487).

According to GB 1,283,737 alkali metal or alkaline earth metal salts of weak acids, both organic and inorganic acids have been found to be especially useful as activators for vinyl acetate catalysts. Sodium, lithium, potassium, rubidium and caesium salts and mixtures thereof are said to have been found to be most effective. However, only potassium acetate is used in the examples.

GB 1,333,449 describes catalysts comprising a carrier impregnated with a palladium salt and a barium carboxylic acid aurate derived from a carboxylic acid having from 2 to 10 carbon atoms, preferably barium aceto-aurate, barium propiono-aurate or barium butyro-aurate. According to GB 1,333,449 the catalysts are prepared by impregnating the carriers with a solution of the active components and drying. GB 1,333,449 does not therefore, describe the preparation of shell impregnated catalysts.

The use of barium auroacetate in catalysts is also described in U.S. Pat. No. 4,370,492.

Canadian patent application CA 2,071.698 describes the use of barium as a component of palladium-containing catalysts in the absence of cadmium and gold. According to CA 2,071.698, the catalytically active substances are applied to the support in customary manner, for example by impregnating the support with a solution of the active substances, subsequently drying it and if appropriate subjecting it to reduction. According to CA 2,071,698 the active substances can also be applied, for example, by precipitation on the support or by spraying on, vapour deposition or dipping. In CA 2,071,698 the preparation processes described in all the examples would be expected to produce non shell type catalysts.

Canadian patent application CA 2,093,610 describes the preparation of shell type catalyst by the steps of (1) dissolving salts of palladium, potassium and (a) cadmium, (b) barium or (c) gold in a solvent; (2) atomising the solution ultrasonically; (3) impregnating the support with the atomised solution one or more times and (4) curing after each impregnation.

It has now been found that a catalyst of high activity is obtained by using a barium salt to precipitate water insoluble palladium and optionally gold compounds on the catalyst support during the production of shell impregnated catalysts.

According to the present invention there is provided a process for preparing a shell impregnated catalyst for use in the production of vinyl acetate from ethylene, acetic acid and an oxygen containing gas, said catalyst comprising palladium and optionally gold deposited on a catalyst support characterised in that the process comprises the steps in sequence of:

(1) impregnating the catalyst support with aqueous solutions of water-soluble palladium and optional gold compounds, (2) contacting the impregnated support from Step (1) with a solution of a barium salt capable of reacting with the water-soluble palladium and optional gold compounds to precipitate water-insoluble palladium and optional gold compounds on the support, (3) converting the precipitated water-insoluble palladium and optional gold compounds formed in Step (2) into palladium and optional gold metal by treatment with a reducing agent, (4) washing the product of Step (3) with water, and (5) contacting the product of Step (4) with a promoter and optionally a barium salt additive and drying the catalyst.

In a further embodiment of the present invention there is provided a process for preparing vinyl acetate which process comprises reacting ethylene with acetic acid in the presence of an oxygen containing gas at a temperature in the range 100° to 200° C. in the presence of the catalyst prepared by the process as herein described.

The catalysts of the present invention have the advantage that they are highly selective towards the production of vinyl acetate at the expense of by-products such as carbon dioxide.

In the preparation of the catalyst of the present invention it is preferred that the catalyst support is a porous silica, alumina, silica/alumina or titania, with silica being most preferred. Preferably, the support has a particle diameter of from about 3 to about 7 mm and a pore volume of from about 0.2 to about 1.5 ml per gram. The support should preferably have a surface area of 50–800 $m^2$ per g.

In the process of the present invention the support is first impregnated with an aqueous solution containing water-soluble palladium and optional gold compounds. Although impregnation of the support with gold compounds is not an essential feature of the present invention, where both palladium and gold compounds are used in the impregnation Step the resulting catalysts have improved productivity.

Palladium (II) chloride, sodium or potassium tetrachloropalladate (II) $Na_2PdCl_4$ or $K_2PdCl_4$, palladium (II) nitrate or palladium (II) sulphate are examples of suitable water-soluble palladium compounds for use in the process of the present invention. Auric (III) chloride or may be used as the water-soluble gold compounds in the process of the present invention. The use of sodium tetrachloropalladate (II) and tetrachloroauric (III) acid is preferred because of their good water solubility and ready availability.

The quantity of palladium compound employed is suitably such as to provide in the final catalyst product from Step (5) 1.65 to 12.5 grams of palladium per litre of catalyst (corresponding to 0.26 to 2.0% by weight depending upon the density of the support), preferably greater than 3.0 grams of palladium per litre of catalyst (corresponding to greater than 0.48% by weight depending upon the density of the support) and more preferably, greater than 3.9 grams per litre of catalyst (corresponding to 0.62% by weight depending upon the density of the support). For palladium/gold catalysts the palladium content is preferably up to 7.5 g/l (corresponding to 1.2% by weight depending upon the density of the support) and for palladium without gold catalysts the palladium content is preferably up to 12.5 g/l (corresponding to 2.0% by weight depending upon the density of the support).

The quantity of gold which may optionally be employed is suitably such as to provide in the final catalyst product from Step (5) from 0.38 to 7.6 grams of gold per litre of catalyst (corresponding to 0.06 to 1.2 % by weight depending upon the density of the support), preferably greater than 1.5 grams per litre of catalyst (corresponding to greater than 0.24% by weight depending upon the density of the support) and most preferably in the range 1.8 to 7.6 grams per litre of catalyst (corresponding to 0.29 to 1.2% by weight depending upon the density of the support). It is preferred that when gold is present in the catalyst, that the weight ratio gold/palladium in the final catalyst product from Step (5) is in the range 0.10 to 1.25, preferably 0.4 to 1.25.

For effective deposition, the volume of solution used for impregnating the support with the palladium or palladium and gold should be from 95 to 100% of the pore volume of the catalyst support, preferably 98 to 99%.

After impregnation, the impregnated support is treated in Step (2), with an aqueous solution of a barium salt preferably, barium hydroxide, capable of reacting with the water-soluble palladium and optional gold compounds to precipitate water-insoluble palladium and optional gold compounds on the support. The amount of barium salt precipitating agent is such that after the solution has been in contact with the impregnated support for between 12 and 24 hours, the pH of the solution is suitably in the range 6.5 to 9.5, preferably 7.5 to 8 when measured at 25° C. During Step (2) of the process of the present invention palladium and optional gold hydroxides are believed to be precipitated or incorporated onto the support.

To convert the water-insoluble palladium and optional gold compounds precipitated in Step (2), into the metallic state, the impregnated support from Step (2) is treated in Step (3), with a reducing agent such as hydrazine, formaldehyde, ethylene or hydrogen. If a gaseous reducing agent is used such as ethylene or hydrogen it will usually be necessary to heat the impregnated support to 100° to 300° C. in order to effect complete reduction.

After the Step (3) described above the reduced material is washed with water (Step (4)), and then impregnated with the required amount of promoter such as alkali metal salt, or alkaline earth metal salt, preferably an acetate and dried (Step (5)). It is preferred that as promoter there is used potassium acetate. Preferably, the promoter content of the final catalyst is in the range 1 to 9% by weight as acetate (corresponding to 6.25 to 56 g/l for potassium acetate depending upon the density of the support).

A barium salt additive such as barium acetate, barium propionate, barium butyrate or barium hydroxide, preferably barium acetate, may also be added in Step (5) preferably in the range 0.1 to 9% by weight as acetate in the final catalyst product from Step (5) (corresponding to 0.6 to 56 g/l depending upon the density of the support). It has been found that by using a barium salt additive, the tendency for catalysts prepared according to the process of the present invention to deactivate with use is reduced. This improvement in catalyst lifetime is also observed for shell type palladium and palladium/gold catalysts prepared using conventional precipitating agents such as sodium metasilicate.

In catalysts prepared according to the process of the present invention using a support having a particle diameter of from about 3 to about 7 mm and a pore volume of from about 0.2 to about 1.5 ml per gram, the palladium and optional gold will be distributed in the outermost 1.0 mm thick layer of the catalyst support.

Preparation of vinyl acetate using the catalysts of the present invention is typically effected by contacting ethylene, acetic acid and an oxygen-containing gas, with a sample of the catalyst at a temperature in the range 100° to 200° C., preferably in the range 140° to 180° C., and at a pressure in the range atmospheric to 20 bar. Typically, the process is carried out heterogeneously with the reactants being present in the gas phase and with levels of oxygen below the limits of flammability. The reaction is usually carried out with an excess of ethylene whilst the amount of acetic acid is determined by dew point considerations. After reaction, the vinyl acetate is separated and purified using conventional methods.

The present invention will now be illustrated with reference to the following Examples and FIGS. 1 to 5 which show in graph form the activities for vinyl acetate production of the catalysts with use.

GENERAL METHOD FOR PREPARING THE CATALYST SAMPLES

During this method only de-ionised water was used.

Step (1) Impregnation of the Support 15 grams of a high surface area spherical silica support having a particle diameter of 4 to 6 mm (KA160 - ex Sud Chemie) was added to 8.7 ml of an aqueous solution of sodium tetrachloropalladate trihydrate [$Na_2PdCl_4 \cdot 3H_2O$] and chloroauric acid trihydrate [$HAuCl_4 \cdot 3H_2O$]. The amounts of the palladium and gold complexes used were such as to achieve the desired palladium and gold loadings on the support. The addition was done in a single portion and the mixture was gently swirled until the solution was fully absorbed (about 2 minutes). After impregnation the impregnated support was allowed to stand for two hours at room temperature.

In the Examples the actual weights of $Na_2PdCl_4 \cdot 3H_2O$ and $HAuCl_4 \cdot 3H_2O$ were selected based upon prior experience within the laboratory to give the required nominal target concentrations of palladium and gold in the finished catalysts. Thus, it was the experience within the laboratory that metals were lost during catalyst preparation. The following empirical equations were determined, based upon observations made during catalyst preparations, to determine the amount of additional palladium and gold required to compensate for these losses.

additional % by weight Pd required=$0.04+0.05a$;

additional % by weight Au required=$0.085-0.21b+(0.48b^2)$ wherein a and b are the % by weight of palladium and gold respectively required in the final catalyst product. For example, for a target of 0.4% by weight gold an extra 0.0778% gold is required to allow for expected losses. Therefore, weights of reagents should be used to achieve 0.478 % by weight gold.

It will, of course, be appreciated that different laboratories and preparation procedures will require different empirical allowances for any metal losses.

In the Examples, the amount of palladium and gold may be calculated in units of grams per litre of catalyst using an average catalyst density of 625 grams per litre.

Step (2) Precipitation

A solution of barium hydroxide (or sodium metasilicate) precipitating agent in 18 ml of water was quickly added to the wet impregnated support to convert the water-soluble palladium and optional gold compounds to water-insoluble palladium and optional gold compounds. The concentration of the barium hydroxide ($Ba(OH)_2$) solution was determined using the following formula:

amount of $Ba(OH)_2$ required (moles)=1.8×[moles of $Na_2PdCl_4$ used +2×(moles of $HAuCl_4$ used) +0.02 millimoles per gram of support used].

The mixture was swirled briefly and was then permitted to stand undisturbed overnight.

Step (3) Reduction

The aqueous phase above the support from Step (2) was treated with a 55% hydrazine hydrate solution (Aldrich) reducing agent to convert the water-insoluble palladium and optional gold compounds formed in Step (2) into palladium and gold metal. The quantity of hydrazine hydrate used was determined using the formula:

22.5×[(moles of $Na_2PdCl_4$ used)+1.5×(moles of $HAuCl_4$ used)]

The mixture was gently swirled then allowed to stand undisturbed overnight.

Step (4) Washing

The aqueous phase was decanted away and the product of Step (3) was washed four times with about 50 ml of water, decanting after each wash. The material was transferred to a glass column fitted with a stopcock and then washed with further water at an approximate rate of one litre per 12 hours until the washings yielded a negative chloride test with silver nitrate.

Step (5) Drying, Promoter Loading and Final Drying

The product from Step (4) was dried at 60° C. overnight in a forced air oven, cooled, then impregnated with a solution of the required amount of potassium acetate promoter and optional barium acetate additive in 8.7 ml of water. No allowance was made for potential metal losses when selecting the amount of potassium acetate promoter and optional barium acetate additive to be used. The mixture was swirled until all the liquid was absorbed, then the catalyst was again dried overnight at 60° C. on a stainless steel screen in a forced-air oven.

When barium hydroxide was used as precipitant, the amount of barium in the finished catalyst, measured by XRF, was greater than that added as barium acetate additive because residual barium from the barium hydroxide preceiptant was also present. The amount of potassium acetate promoter in the finished catalyst was measured to an accuracy of±10% by XRF.

Catalyst Test Method

Tests were performed at 7.8 barg and 150° C. using 2.5g samples of the catalyst pellets, diluted with 60 ml of 1 mm glass beads and loaded into a stainless steel tube of internal diameter 10–11 mm. The catalyst was activated at 7.8 barg by heating at 160° C. for 3 hours in a stream of nitrogen and then at 150° C. for 10 minutes in a stream of ethylene. Acetic acid vapour was then mixed with the ethylene and passed over the catalyst for a period of at least 50 minutes. A mixture of 21% oxygen in helium was gradually added to the feed gas while maintaining the maximum catalyst bed temperature at 150° C. The catalyst hot spot was maintained at 150° C. The final composition of the reactant mixture was ethylene:acetic acid: oxygen: helium=53.1: 10.4: 7.7: 28.6 by volume and the total gas hourly space velocity was 3850 $hr^{-1}$ The product stream was analysed in the vapour phase at hourly intervals by means of an on-line gas-liquid chromatograph.

Activity of the catalyst was calculated as grams of vinyl acetate produced per litre of catalyst per hour (space time yield, STY) and selectivity of the catalyst was calculated as the percentage of converted ethylene present in the product. Data are reported on the basis of the average of activities and selectivities measured between 17 and 22 hours after full oxygen content was achieved.

The results of the experiments are summarised in Table 1 below. The activities of the catalysts with use are shown in FIGS. 1 to 5.

EXAMPLE 1—CATALYST (G)

Figure 1:
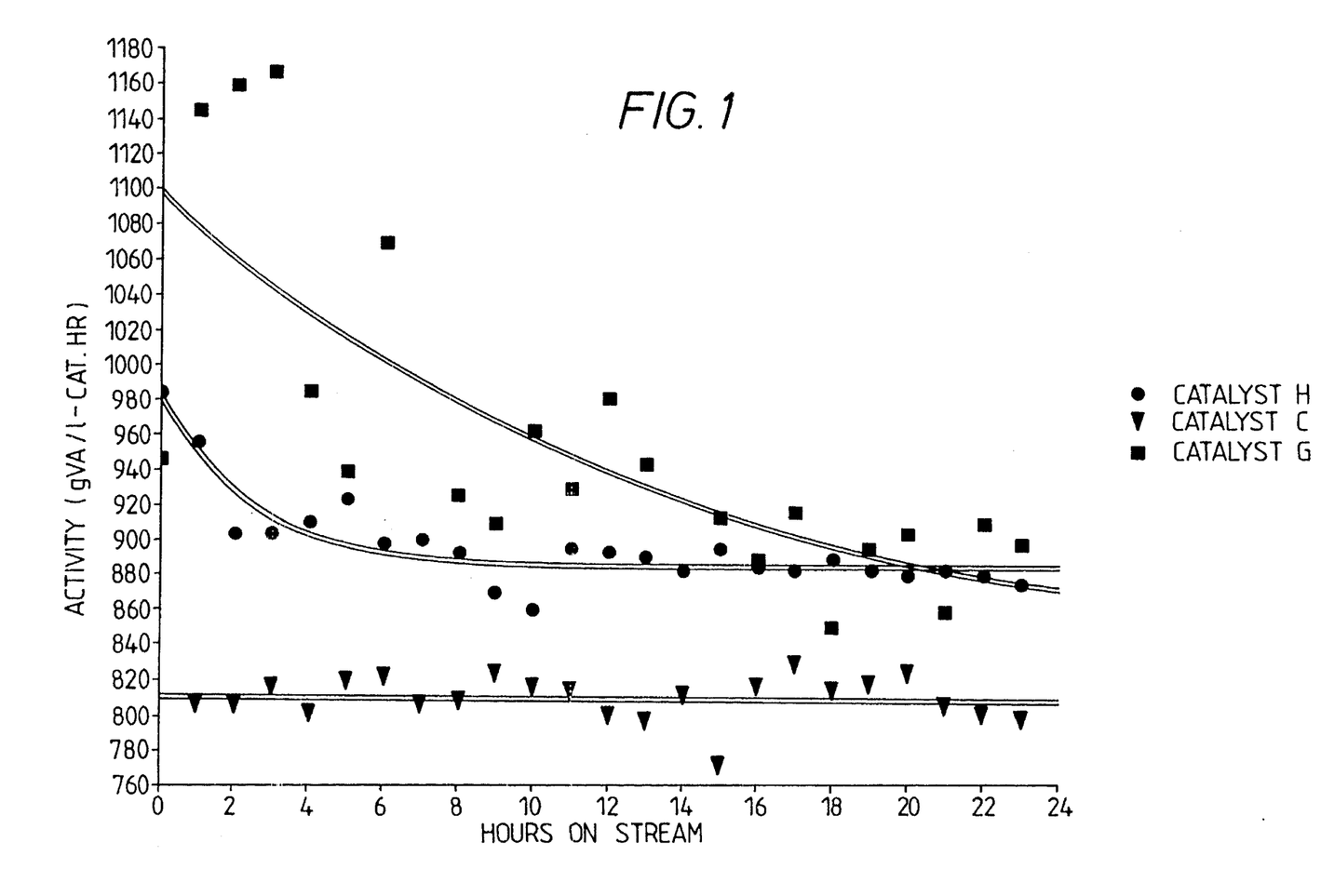

A catalyst was prepared to have a nominal target composition of 0.9 % by weight palladium (5.62 g/l) and 0.4 % by weight gold (2.50 g/l) according to the general method described above using 0.5529 g of $Na_2PdCl_4.3H_2O$ and 0.1561 g of $HAuCl_4.3H_2O$ in Step (1); 1.4845 g of $Ba(OH)_2$ in Step (2); 2.76 g of 55% hydrazine hydrate solution in Step (3) and 1.15g of potassium acetate (corresponding to about 7% by weight, 43.8 g/l in the final catalyst product) as promoter in Step (5). The catalyst was found to have an average activity of 888 grams of vinyl acetate per litre of catalyst per hour (at 17 to 22 hours after full oxygen content was achieved) and the activity of the catalyst with use is shown in FIG. 1.

Comparative Example (a)—Catalyst (A)

Figure 3:
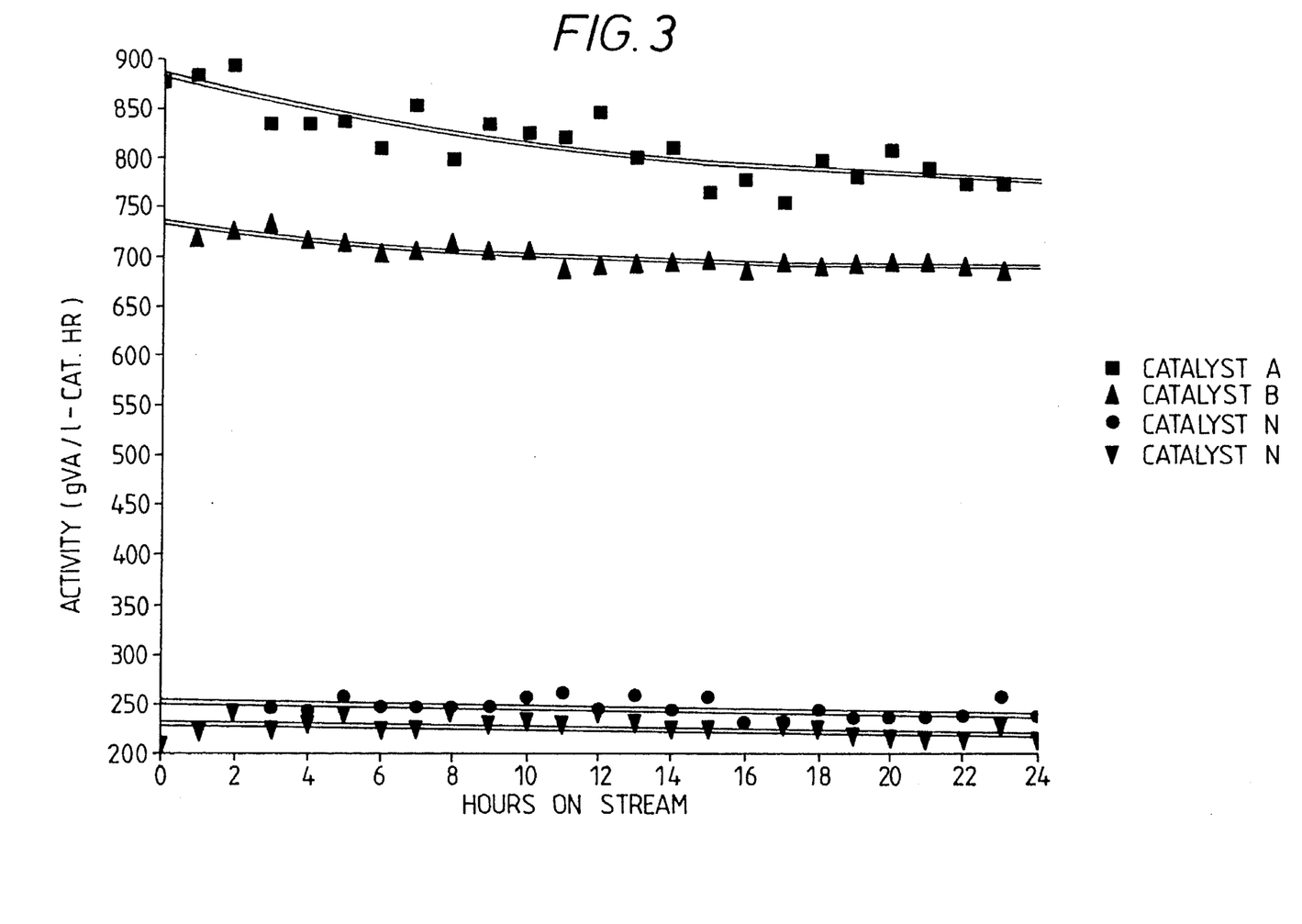

A catalyst was prepared according to Example 1 except that 0.99 g of sodium silicate pentahydrate was used in place of $Ba(OH)_2$ in Step (2). The catalyst was found to have an activity of 784 grams of vinyl acetate per litre of catalyst per hour. Comparison with Catalyst (G) in Example 1 shows the benefit of the present invention of using a barium salt as precipitating agent in the preparation of a palladium/gold shell type catalyst. The activity of the catalyst with use is shown in FIG. 3.

EXAMPLE 2—CATALYST (H)

A catalyst was prepared according to Example 1 except that only 0,825 g (corresponding to about 5.1%, 31.9 g/l by weight in the final catalyst product) of potassium acetate were used as promoter in Step (5). The catalyst was found to have an average activity of 881 grams of vinyl acetate per litre of catalyst per hour. The activity of the catalyst with use is shown in FIG. 1.

EXAMPLE 3—CATALYST (J)

A catalyst was prepared according to Example 1 except that 0,742 g of barium hydroxide was used as precipitating agent in Step (2). The catalyst was found to have an average activity of 837 grams of vinyl acetate per litre of catalyst per hour (at 17 to 22 hours after full oxygen content was achieved).

EXAMPLE 4—CATALYST (K)

Example 1 was repeated using 2,969 g of barium hydroxide in Step (2). Average activity was 495 grams of vinyl acetate per litre of catalyst per hour. The results for Examples 1, 3 and 4 indicate that as the amount of barium hydroxide precipitating agent used in Step (2) is increased the beneficial effect on average activity passes through a maximum.

EXAMPLE 5—CATALYST (I)—PALLADIUM CATALYST

Figure 2:
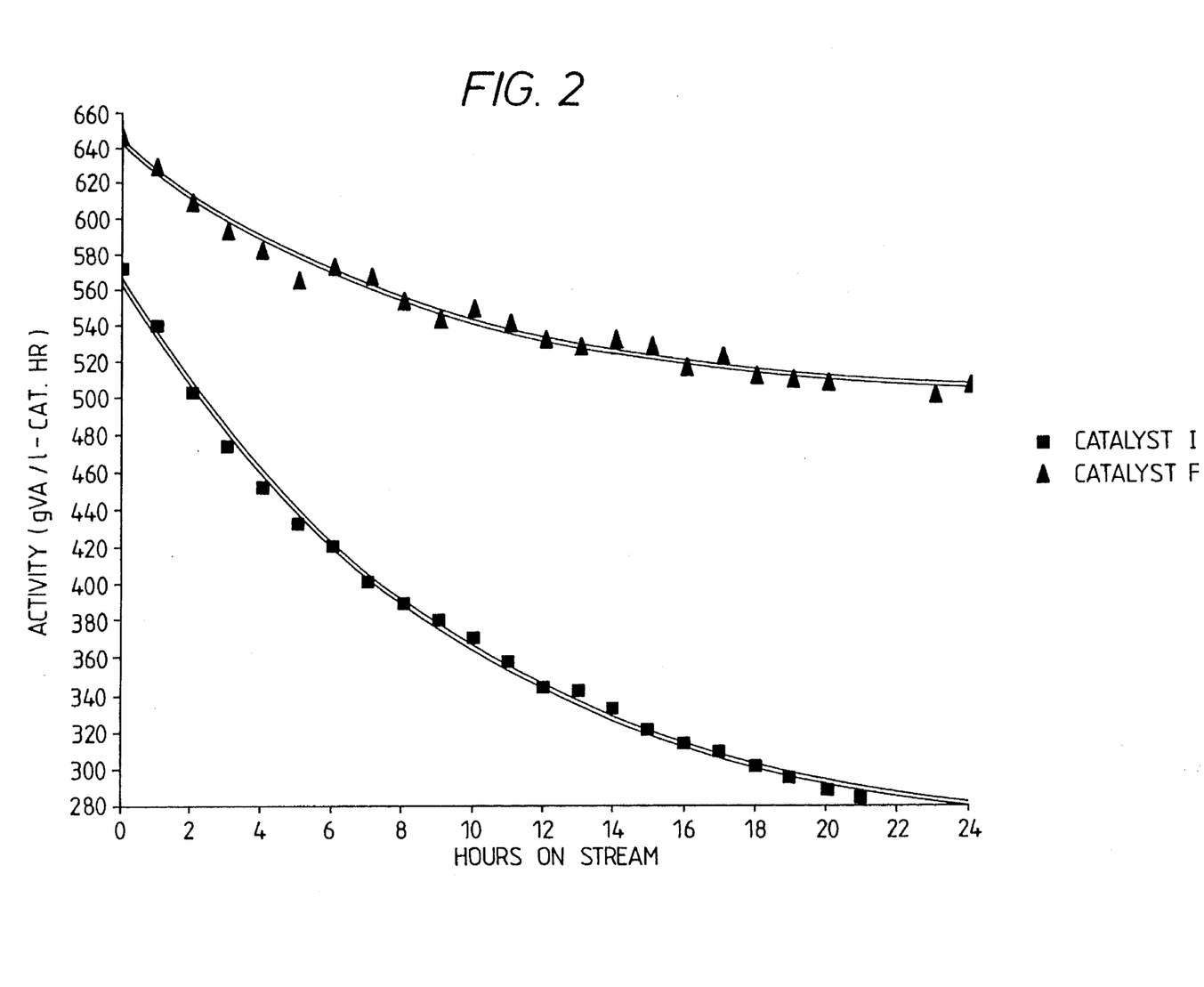

A catalyst was prepared according to Example 1 except that $HAuCl_4.3H_2O$ was omitted in Step (1). The catalyst was found to have an average activity of 299 STY. The activity of the catalyst with use is shown in FIG. 2.

Comparative Example (b)—Catalyst (D)

Figure 4:
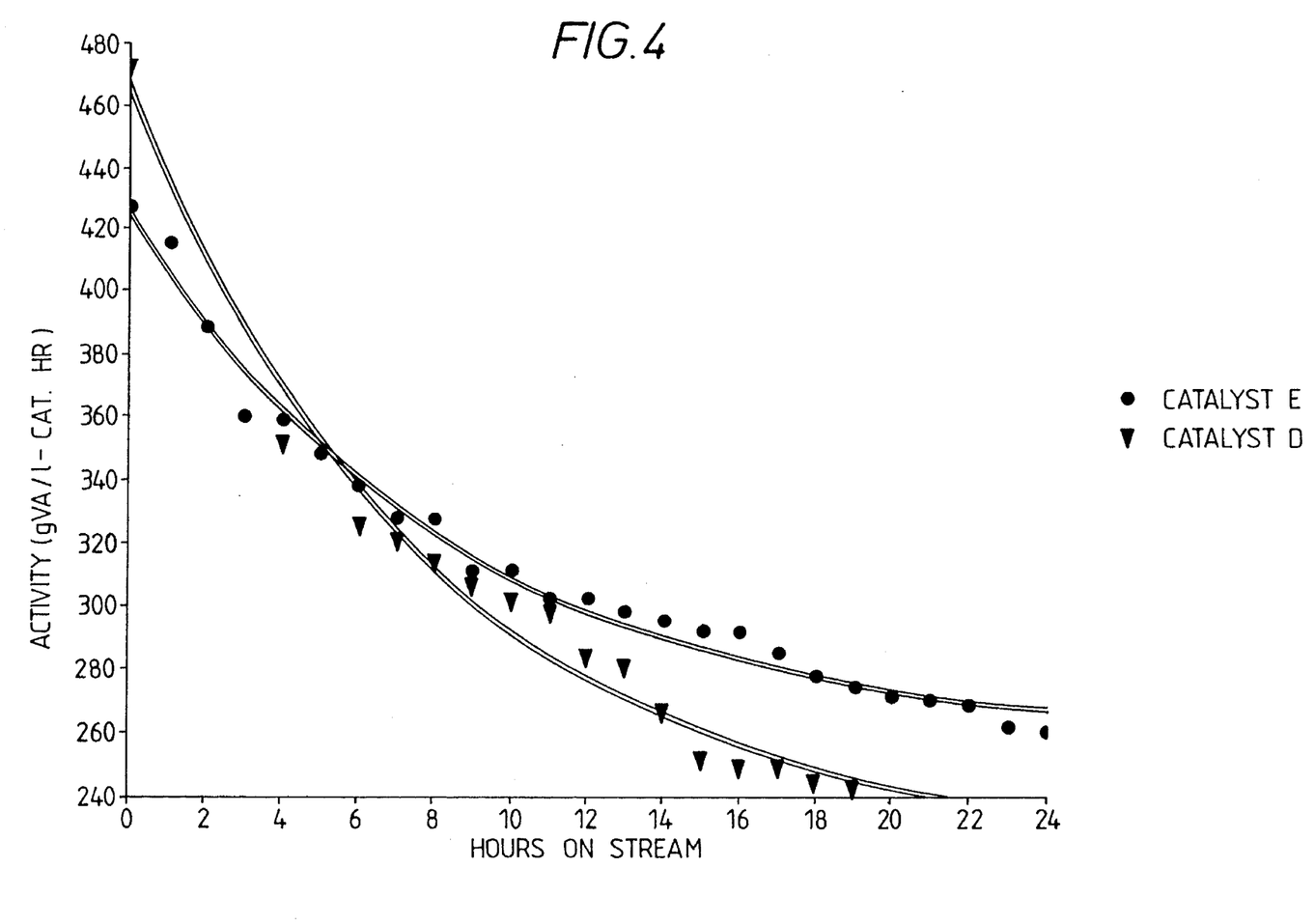

A catalyst was prepared according to Example 5 except that 0.99 g of sodium metasilicate pentahydrate was used as precipitating agent in place of barium hydroxide in Step (2). The catalyst was found to have an average activity of 247 grams of vinyl acetate per litre of catalyst per hour. Comparison with Catalyst (I) in Example 5 shows the benefit of the present invention of using a barium salt as precipitating agent in the preparation of a palladium only (rather than palladium/gold) shell type catalyst. The activity of the catalyst with use is shown in FIG. 4.

EXAMPLE 6—CATALYST (C)—BARIUM ACETATE ADDITIVE

A catalyst was prepared according to Example 1 except that a mixture of 0.825 g (corresponding to about 5.1% by weight, 31.9 g/l in the final catalyst product) of potassium acetate promoter and 0.795 g (corresponding to about 4.7% by weight, 29.8 g/l in the final catalyst product) of barium acetate additive was used in Step (5). The pH of the solution above the support after completion of precipitation Step (2) was measured to be 8. The catalyst was found to have an average activity of 814 grams of vinyl acetate per litre of catalyst per hour. The catalyst was analysed by XRF and was found to contain by weight 0.88% palladium; 0.45% gold; 1.71% potassium and 3.90% barium. The effect of the barium additive of reducing the rate of deactivation with use is shown in FIG. 1.

Comparative Example (c)—Catalyst (B)

A catalyst was prepared according to Example 6 except that 0.99 g of sodium metasilicate pentahydrate was used as precipitating agent in place of barium hydroxide in Step (2). The catalyst was analysed by XRF and was found to contain by weight 0.91% palladium; 0.41% gold; 1.77% potassium and 2.60% barium. The catalyst was found to have an average activity of 693 grams of vinyl acetate per litre of catalyst per hour. Comparison with Catalyst (C) in Example 6 shows the benefit of using a barium salt as precipitating agent in the preparation of a palladium/gold shell type catalyst which has potassium acetate promoter and barium acetate additive. The activity of the catalyst with use is shown in FIG. 3.

EXAMPLE 7—CATALYST (F)—BARIUM ACETATE ADDITIVE; PALLADIUM ONLY

A catalyst was prepared according to Example 6 except that $HAuCl_4.3H_2O$ was omitted in Step (1). The catalyst was analysed by XRF and was found to contain by weight 0.94% palladium; 1.74% potassium and 4.10% barium. The catalyst was found to have an activity of 513 grams of vinyl acetate per litre of catalyst per hour. The effect of the barium additive of reducing the rate of deactivation with use is shown in FIG. 2.

Comparative Example (d)—Catalyst (E)

A catalyst was prepared according to Example 7 except that 0.99 g of sodium metasilicate pentahydrate precipitating agent was used in place of barium hydroxide in Step (2). The catalyst was analysed by XRF and was found to contain by weight 0.88% palladium; 1.91% potassium and 2.70% barium. The catalyst was found to have an activity of 274 grams of vinyl acetate per litre of catalyst per hour (an 87.2% decrease in activity compared with Example 7). This shows the benefit of using a barium salt as precipiting agent in the preparation of a palladium only shell type catalyst which has potassium acetate promoter and barium acetate additive. The activity of the catalyst with use is shown in FIG. 4.

Comparative Example (e)—Catalyst (N)

A catalyst was prepared according to Comparative Example (a) except that 2.9823 g of barium acetate additive was used in Step (5) and no potassium acetate promoter was used. Two experiments were performed with this catalyst to produce vinyl acetate. The activity of the catalyst with use is shown in FIG. 3, which shows that despite the lower activity, the rate of deactivation is less than for corresponding catalyst (A) with potassium acetate promoter alone.

EXAMPLE 8—CATALYST (L)

Figure 5:
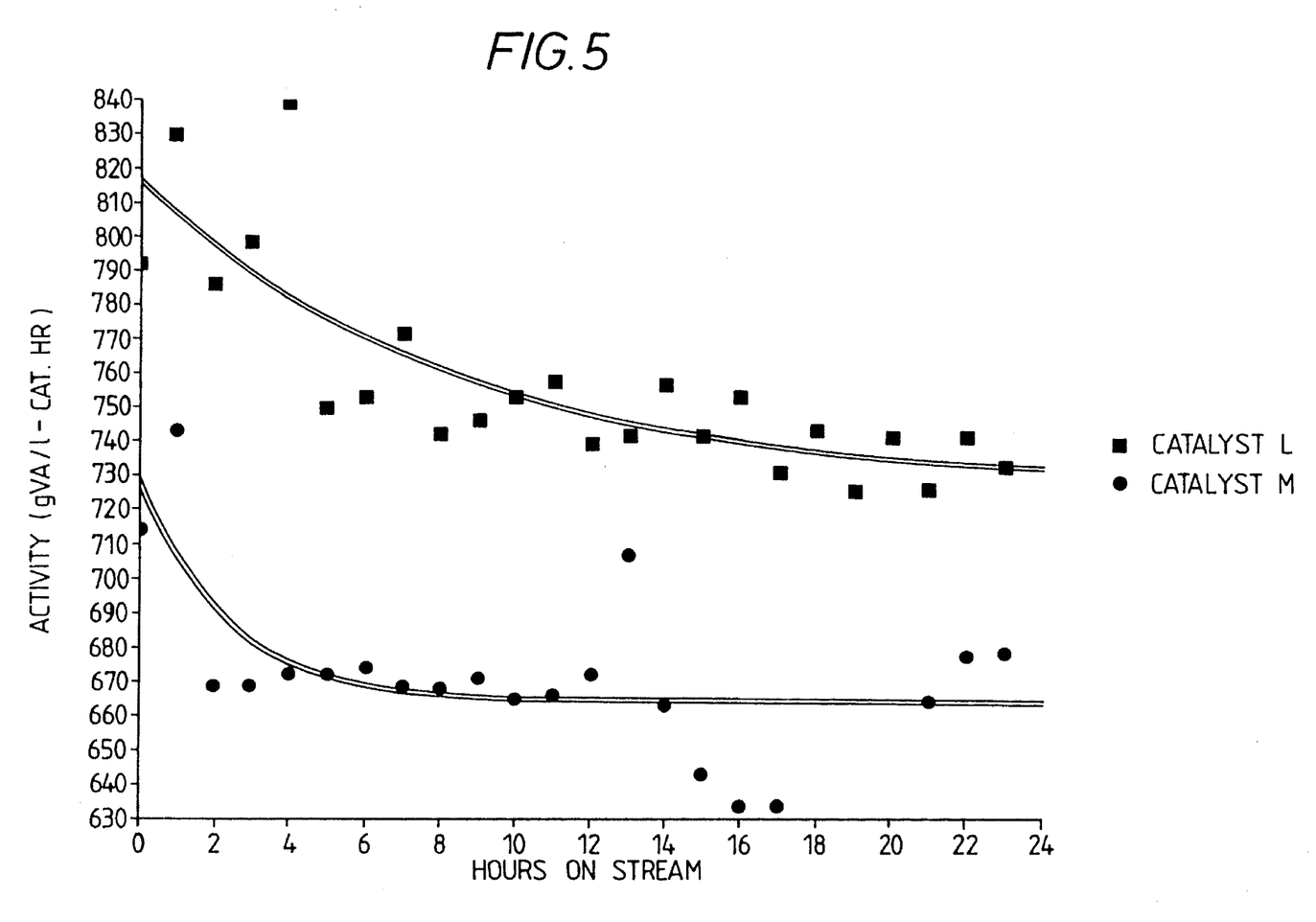

A catalyst was prepared according to the general procedure described above to have a nominal target composition by weight of 0.7% palladium (4.38 g/l) and 0.308% gold (1.92 g/l) using 0.4343 g of $Na_2PdCl_4.3H_2O$ and 0.1219 g of $HAuCl_4.3H_2O$ in Step (1); 1.1963 g of barium hydroxide in Step (2); 2.16 g of 55% hydrazine hydrate solution in Step (3) and 1.15 g (corresponding to about 7% by weight in the final catalyst product) of potassium acetate as promoter in Step (5). The catalyst was found to have an average activity of 737 grams of vinyl acetate per litre of catalyst per hour and a selectivity of 94.0%(at 17 to 22 hours after full oxygen content was achieved). The activity with use is shown in FIG. 5.

EXAMPLE 9—CATALYST (M)

A catalyst was prepared according to Example 8 except that 0.72 g (corresponding to about 4.5% by weight, 28.1 g/l in the final catalyst product)of potassium acetate promoter and 0.48 g (corresponding to about 3% by weight, 18.8 g/l in the final catalyst product) of barium acetate additive was used in Step (5). The catalyst was found to have an average activity of 641 grams of vinyl acetate per litre of catalyst per hour and a selectivity of 93.5%(at 17 to 22 hours after full oxygen content was achieved). The activity with use is shown in FIG. 5.

The average activities and selectivities of the catalysts are given in Table 1. The results show the benefits of using a barium salt as precipitant over sodium metasilicate for palladium and palladium/gold catalysts and also for potassium acetate promoted catalysts with and without barium acetate additive.

The activities of the catalysts with use are shown in FIGS. 1 to 5. These show that barium acetate additive reduces the rate of deactivation of (a) palladium/gold shell type catalysts with barium salt precipitant in FIGS. 1 and 5; (b) palladium only shell type catalysts with barium salt precipitant in FIG. 2; (c) palladium/gold shell type catalysts with sodium metasilicate precipitant in FIG. 3; (d) palladium only shell type catalysts with sodium metasilicate precipitant in FIG. 4.

TABLE 1

| Expt. | Cat. | Metal(s) | Precipitant | Promoter/ Additive | Averages between 17–22 Hours on stream | | STY When full oxygen content achieved | STY 24th Hour | Decrease |
|---|---|---|---|---|---|---|---|---|---|
| | | | | | STY | Selectivity | | | |
| 1 | G | Pd/Au | Ba(OH)$_2$ | K | 888 | 91.5 | 946[2] | 897 | 49 |
| 2 | H | Pd/Au | Ba(OH)$_2$ | K | 881 | 91.3 | 984 | 873 | 111 |
| 3 | J | Pd/Au | Ba(OH)$_2$ | K | 837 | 92.3 | — | — | — |
| 4 | K | Pd/Au | Ba(OH)$_2$ | K | 495 | 95.0 | — | — | — |
| 8 | L | Pd/Au | Ba(OH)$_2$ | K | 737 | 94.0 | — | — | — |
| 6 | C | Pd/Au | Ba(OH)$_2$ | K/Ba | 814 | 93.2 | 807 | 797 | 10 |
| 9 | M | Pd/Au | Ba(OH)$_2$ | K/Ba | 641 | 93.5 | — | — | — |
| 5 | I | Pd | Ba(OH)$_2$ | K | 299 | 95.5 | 572 | 284[1] | 288 |
| 7 | F | Pd | Ba(OH)$_2$ | K/Ba | 513 | 93.8 | 648 | 502 | 146 |
| (a) | A | Pd/Au | Namsil | K | 784 | 93.1 | 877 | 774 | 103 |
| (c) | B | Pd/Au | Namsil | K/Ba | 693 | 92.6 | 735 | 687 | 48 |
| (b) | D | Pd | Namsil | K | 247 | 95.6 | 472 | 242[1] | 230 |
| (d) | E | Pd | Namsil | K/Ba | 274 | 90.0 | 428 | 262 | 166 |
| (e) | N | Pd/Au | Namsil | Ba | 236 | 91.0 | 245[3] | 237 | 8 |
| | | | | | 217 | 89.3 | 206 | 210 | (−4) |

Namsil = Sodium metasilicate
[1]measured at 21st hour, STY at 24th hour expected to be lower
[2]start-up erratic, expect initial STY to be about 1095 implying decrease about 198
[3]measured at 3rd hour

We claim:

1. A process for the production of vinyl acetate which comprises contacting ethylene, acetic acid and an oxygen-containing gas, at a temperature in the range 100° to 200° C. and at a pressure in the range atmospheric to 20 bar, with a shell impregnated catalyst comprised of palladium and optionally gold deposited on a catalyst support which is prepared by a process comprising the steps in sequence of:

(1) impregnating the catalyst support with aqueous solutions of water-soluble palladium and optional gold compounds, (2) contacting the impregnated support from Step (1) with a solution of a barium salt capable of reacting with the water-soluble palladium and optional gold compounds to precipitate water-insoluble palladium and optional gold compounds on the support, (3) converting the precipitated water-insoluble palladium and optional gold compounds formed in Step (2) into palladium and optional gold metal by treatment with a reducing agent, (4) washing the product of Step (3) with water, and (5) contacting the product of Step (4) with a promoter and optionally a barium salt additive and drying the catalyst.

2. A process as claimed in claim 1 in which the barium salt used in Step (2) comprises barium hydroxide.

3. A process as claimed in claim 1 in which the amount of barium salt used in Step (2) is selected so that after the impregnated support has been in contact with the solution of barium salt for between 12 and 24 hours, the pH of the solution is in the range 6.5 to 9.5 measured at 25° C.

4. A process as claimed in claims 1 in which in Step (1) the catalyst support is impregnated with a solution of a quantity of water-soluble palladium compound such as to provide 1.65 to 12.5 grams palladium per litre of final catalyst product in Step (5).

5. A process as claimed in claim 1 in which in Step (1), the catalyst support is impregnated with a solution of a quantity of water-soluble gold compound such as to provide 0.38 to 7.6 grams gold per litre of final catalyst product in Step (5).

6. A process as claimed in claim 4 in which Step (1), the catalyst support is impregnated with a solution of a quantity of water-soluble gold compound such as to provide 0.38 to 7.6 grams gold per litre of final catalyst product in Step (5).

7. A process as claimed in claim 6 in which the support comprises silica having a particle diameter of from about 3 to about 7 mm, a pore volume of from about 0.2 to about 1.5 ml per gram and a surface area of 50–800 $m^2$ per g.

8. A process as claimed in claim 1 in which in Step (5), there is used a barium salt additive in an amount to provide in the range 0.1 to 9% by weight as acetate in the final catalyst product.

9. A process as claimed in claim 4 in which in Step (5), there is used a barium salt additive in an amount to provide in the range 0.1 to 9% by weight as acetate in the final catalyst product.

10. A process as claimed in claim 6 in which in Step (5), there is used a barium salt additive in an amount to provide in the range 0.1 to 9% by weight as acetate in the final catalyst product.

11. A process as claimed in claim 7 in which in Step (5), there is used a barium salt additive in an amount to provide in the range 0.1 to 9% by weight as acetate in the final catalyst product.

12. A process as claimed in claim 11 in which the barium salt additive comprises barium acetate.

13. A process as claimed in claim 7 in which in Step (5) potassium acetate is used as promoter in an amount to provide in the range 1 to 9% by weight as acetate in the final catalyst product.

14. A process as claimed in claim 11 in which in Step (5) potassium acetate is used as promoter in an amount to provide in the range 1 to 9% by weight as acetate in the final catalyst product.

15. A process for the production of vinyl acetate which comprises preparing a shell impregnated catalyst comprised of palladium and optionally gold deposited on a catalyst support by a process comprising the steps in sequence of:
  (1) impregnating the catalyst support with aqueous solutions of water-soluble palladium and optional gold compounds,
  (2) contacting the impregnated support from step 1 with a solution of a barium salt capable of reacting with the water-soluble palladium and optional gold compounds to precipitate water-insoluble palladium and optional gold compounds on the support,
  (3) converting the precipitated water-insoluble palladium and optional gold compounds formed in step 2 and to palladium and optional gold metal by treatment with a reducing agent,
  (4) washing the product of step 3 with water, and
  (5) contacting the product of step 4 with a promoter and optionally a barium salt additive and drying at the catalyst;

and contacting ethylene, acetic acid and an oxygen containing gas, at a temperature in the range of 100° to 200° C. and at a pressure in the range of atmospheric to 20 bar, in the presence of said catalyst.

* * * * *